United States Patent
Park et al.

(10) Patent No.: US 11,467,148 B2
(45) Date of Patent: Oct. 11, 2022

(54) METHOD AND APPARATUS FOR ANALYZING COMMUNICATION ENVIRONMENTS AND DESIGNING NETWORKS IN CONSIDERATION OF TREES

(71) Applicant: Samsung Electronics Co., Ltd., Suwon-si (KR)

(72) Inventors: Jungmin Park, Seoul (KR); Byungchul Kim, Seongnam-si (KR); Youngju Lee, Seoul (KR); Dongkyu Choi, Seongnam-si (KR); Junghwan Choi, Yongin-si (KR); Seungku Han, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1057 days.

(21) Appl. No.: 16/137,026

(22) Filed: Sep. 20, 2018

(65) Prior Publication Data
US 2019/0094196 A1 Mar. 28, 2019

Related U.S. Application Data

(60) Provisional application No. 62/563,892, filed on Sep. 27, 2017.

(30) Foreign Application Priority Data

Jan. 22, 2018 (KR) ........................ 10-2018-0007780

(51) Int. Cl.
*H04B 17/30* (2015.01)
*G01N 33/00* (2006.01)
(Continued)

(52) U.S. Cl.
CPC ........ *G01N 33/0098* (2013.01); *G01S 7/4802* (2013.01); *H04B 17/101* (2015.01); *H04B 17/391* (2015.01); *H04B 17/3912* (2015.01)

(58) Field of Classification Search
CPC ................ H04B 17/101; H04B 17/391; H04B 17/3912; H04B 17/30; G01N 33/0098
See application file for complete search history.

(56) References Cited

U.S. PATENT DOCUMENTS 7,868,817 B2 1/2011 Meyers et al.
2010/0103868 A1* 4/2010 Meng .................... H04W 16/18
370/328
(Continued)

FOREIGN PATENT DOCUMENTS

CA 2 925 632 A1 9/2016
CN 101137166 A 3/2008
(Continued)

OTHER PUBLICATIONS

Chinese Office Action dated Nov. 3, 2021, issued in Chinese Patent Application No. 201880061821.2.
(Continued)

*Primary Examiner* — Blane J Jackson
(74) *Attorney, Agent, or Firm* — Jefferson IP Law, LLP

(57) ABSTRACT

A method for identifying radio signal transmission characteristics in a wireless communication system and an apparatus therefor are provided. The method may include identifying a signal transmission site, identifying a signal reception site, finding an area where a tree is present between the signal transmission site and the signal reception site, checking characteristics of the crown of the tree and characteristics of the trunk of the tree, and examining transmission characteristics of a radio signal sent from the signal transmission site to the signal reception site on the basis of the characteristics of the crown and the trunk. The (Continued)

method and apparatus relate to a communication method and system for converging a 5th-Generation (5G) communication system for supporting higher data rates beyond a 4th-Generation (4G) system with a technology for internet of things (IoT), and may be applied to intelligent services based on the 5G communication and the IoT-related technologies.

18 Claims, 14 Drawing Sheets

(51) Int. Cl.
*H04B 17/10* (2015.01)
*G01S 7/48* (2006.01)
*H04B 17/391* (2015.01)

(56) References Cited

U.S. PATENT DOCUMENTS

| | | |
|---|---|---|
| 2011/0143772 A1 | 6/2011 | Sridhara et al. |
| 2011/0287801 A1 | 11/2011 | Levin et al. |
| 2013/0278465 A1 | 10/2013 | Owen |
| 2013/0278466 A1 | 10/2013 | Owen |
| 2014/0070991 A1 | 3/2014 | Liu et al. |
| 2014/0243012 A1* | 8/2014 | Wirola ............... G01S 5/0236 455/456.1 |
| 2015/0341886 A1 | 11/2015 | Miller et al. |
| 2016/0358190 A1* | 12/2016 | Terrazas ............... G06F 16/29 |
| 2017/0019797 A1* | 1/2017 | Rubio ............... G06V 10/457 |
| 2017/0301104 A1* | 10/2017 | Qian ............... G01C 21/005 |
| 2018/0138996 A1 | 5/2018 | Lee et al. |
| 2018/0278349 A1* | 9/2018 | Zhihua ............... H04B 17/3913 |
| 2019/0342763 A1 | 11/2019 | Jung et al. |

FOREIGN PATENT DOCUMENTS

| | | |
|---|---|---|
| CN | 103580762 A | 2/2014 |
| EP | 1746747 B1 | 1/2007 |
| EP | 3 509 231 A1 | 7/2019 |
| GB | 2530272 A | 3/2016 |
| KR | 10-2018-0055622 A | 5/2018 |
| WO | 1998/04059 A1 | 1/1998 |

OTHER PUBLICATIONS

International Search Report dated Jan. 10, 2019; International Application #. PCT/KR2018/011158.
Schubert F M et al:"Modeling of multipath propagation components caused by trees and forests", Antennas and Propagation (EUCAP), 2010 Proceedings of the Fourth European Conference on, IEEE, Piscataway, NJ, USA, Apr. 12, 2010 (Apr. 12, 2010), pp. 1-5, XP031705398, Apr. 12, 2010.
Jung-Min Lee et al: "Simple statistical model of scattering by tree for site-specific channel model for wireless communication applications",Geoscience and Remote Sensing Symposium, 2005. IGARSS '05. Proceedings . 2005 IEEE International Seoul, Korea Jul. 25-29, 2005, Piscataway, NJ, USA,IEEE, vol. 1, Jul. 25, 2005 (Jul. 25, 2005), pp. 570-573, XP010849043, Jul. 25, 2005.
Extended European Search Report dated Jun. 22, 2020, issued in European Patent Office Application No. 18860523.2.
Indian Office Action dated Mar. 16, 2022, issued in Indian Application No. 202017009045.

* cited by examiner

METHOD AND APPARATUS FOR ANALYZING COMMUNICATION ENVIRONMENTS AND DESIGNING NETWORKS IN CONSIDERATION OF TREES

CROSS-REFERENCE TO RELATED APPLICATION(S)

This application is based on and claims priority under 35 U.S.C. § 119(e) of a U.S. Provisional application Ser. No. 62/563,892, filed on Sep. 27, 2017, in the U.S. Patent and Trademark Office, and under 35 U.S.C. § 119(a) of a Korean patent application number 10-2018-0007780, filed on Jan. 22, 2018, in the Korean Intellectual Property Office, the disclosure of which is incorporated by reference herein in its entirety.

BACKGROUND

1. Field

The disclosure relates to a method and apparatus for modeling a radio communication environment for a wireless communication system and operating networks based on the modeling results. More particularly, the disclosure relates to a method and apparatus for modeling a communication environment in consideration of the locations and characteristics of trees and operating networks based on the modeling results in a wireless communication environment using mmWave bands.

2. Description of Related Art

To meet the demand for wireless data traffic having increased since deployment of 4th-Generation (4G) communication systems, efforts have been made to develop an improved 5th-Generation (5G) or pre-5G communication system. Therefore, the 5G or pre-5G communication system is also called a 'Beyond 4G Network' or a 'Post LTE System'. The 5G communication system is considered to be implemented in higher frequency (mmWave) bands, e.g., 60 GHz bands, so as to accomplish higher data rates. To decrease propagation loss of the radio waves and increase the transmission distance, the beamforming, massive multiple-input multiple-output (MIMO), full dimensional MIMO (FD-MIMO), array antenna, an analog beam forming, large scale antenna techniques are discussed in 5G communication systems. In addition, in 5G communication systems, development for system network improvement is under way based on advanced small cells, cloud radio access networks (RANs), ultra-dense networks, device-to-device (D2D) communication, wireless backhaul, moving network, cooperative communication, coordinated multi-points (CoMP), reception-end interference cancellation and the like. In the 5G system, hybrid FSK and QAM modulation (FQAM) and sliding window superposition coding (SWSC) as an advanced coding modulation (ACM), and filter bank multi carrier (FBMC), non-orthogonal multiple access (NOMA), and sparse code multiple access (SCMA) as an advanced access technology have been developed.

The Internet, which is a human centered connectivity network where humans generate and consume information, is now evolving to the Internet of Things (IoT) where distributed entities, such as things, exchange and process information without human intervention. The Internet of Everything (IoE), which is a combination of the IoT technology and the big data processing technology through connection with a cloud server, has emerged. As technology elements, such as "sensing technology", "wired/wireless communication and network infrastructure", "service interface technology", and "Security technology" have been demanded for IoT implementation, a sensor network, a machine-to-machine (M2M) communication, machine type communication (MTC), and so forth have been recently researched. Such an IoT environment may provide intelligent Internet technology services that create a new value to human life by collecting and analyzing data generated among connected things. IoT may be applied to a variety of fields including smart home, smart building, smart city, smart car or connected cars, smart grid, health care, smart appliances and advanced medical services through convergence and combination between existing information technology (IT) and various industrial applications.

In line with this, various attempts have been made to apply 5G communication systems to IoT networks. For example, technologies such as a sensor network, machine type communication (MTC), and machine-to-machine (M2M) communication may be implemented by beamforming, MIMO, and array antennas. Application of a cloud Radio Access Network (RAN) as the above-described Big Data processing technology may also be considered to be as an example of convergence between the 5G technology and the IoT technology.

As described above, recent communication systems tend to use relatively high frequency communication signals. Hence, there is a need to analyze radio communication environments in consideration of the trees and to configure and operate networks based on the analysis results.

The above information is presented as background information only to assist with an understanding of the disclosure. No determination has been made, and no assertion is made, as to whether any of the above might be applicable as prior art with regard to the disclosure.

SUMMARY

Aspects of the disclosure are to address at least the above problems and/or disadvantages and to provide at least the advantages described below. Accordingly, an aspect of the disclosure is to provide a method and apparatus that support modeling of a radio communication environment and utilization of the modeling results to enable a wireless communication system to operate in consideration of trees. Another aspect of the disclosure is to provide a method and apparatus that analyze and simulate radio signal propagation paths by modeling characteristics of trees and radio signals sent from the transmitter in a communication system using radio waves, and enable network design and operation based on the simulation results.

In accordance with an aspect of the disclosure, a method for identifying radio signal transmission characteristics in a wireless communication system is provided. The method includes identifying a signal transmission location, identifying a signal reception location, identifying an area where a tree is present between the signal transmission location and the signal reception location, identifying a characteristic of the crown of the tree and a characteristic of the trunk of the tree, and determining a transmission characteristic of a radio signal sent from the signal transmission location to the signal reception location based on the characteristic of the crown and the characteristic of the trunk.

In accordance with another aspect of the disclosure, a computing device capable of identifying signal transmission characteristics in a wireless communication system is provided. The computing device includes a transceiver for transmitting and receiving information, and at least one processor connected with the transceiver and configured to identify a signal transmission location, identify a signal reception location, identify an area where a tree is present between the signal transmission location and the signal reception location, identify a characteristic of a crown of the tree and a characteristic of a trunk of the tree, and determine a transmission characteristic of a radio signal sent from the signal transmission location to the signal reception location based on the characteristic of the crown and the characteristic of the trunk.

In a feature of the disclosure, the proposed method and apparatus enable readily determination of propagation characteristics of a radio signal in a wireless communication system. Hence, it is possible to support more accurate system design and network operation based on the determined characteristics.

Additional aspects will be set forth in part in the description which follows and, in part, will be apparent from the description, or may be learned by practice of the presented embodiments.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

The same reference numerals are used to represent the same elements throughout the drawings.

DETAILED DESCRIPTION

Figure 1:
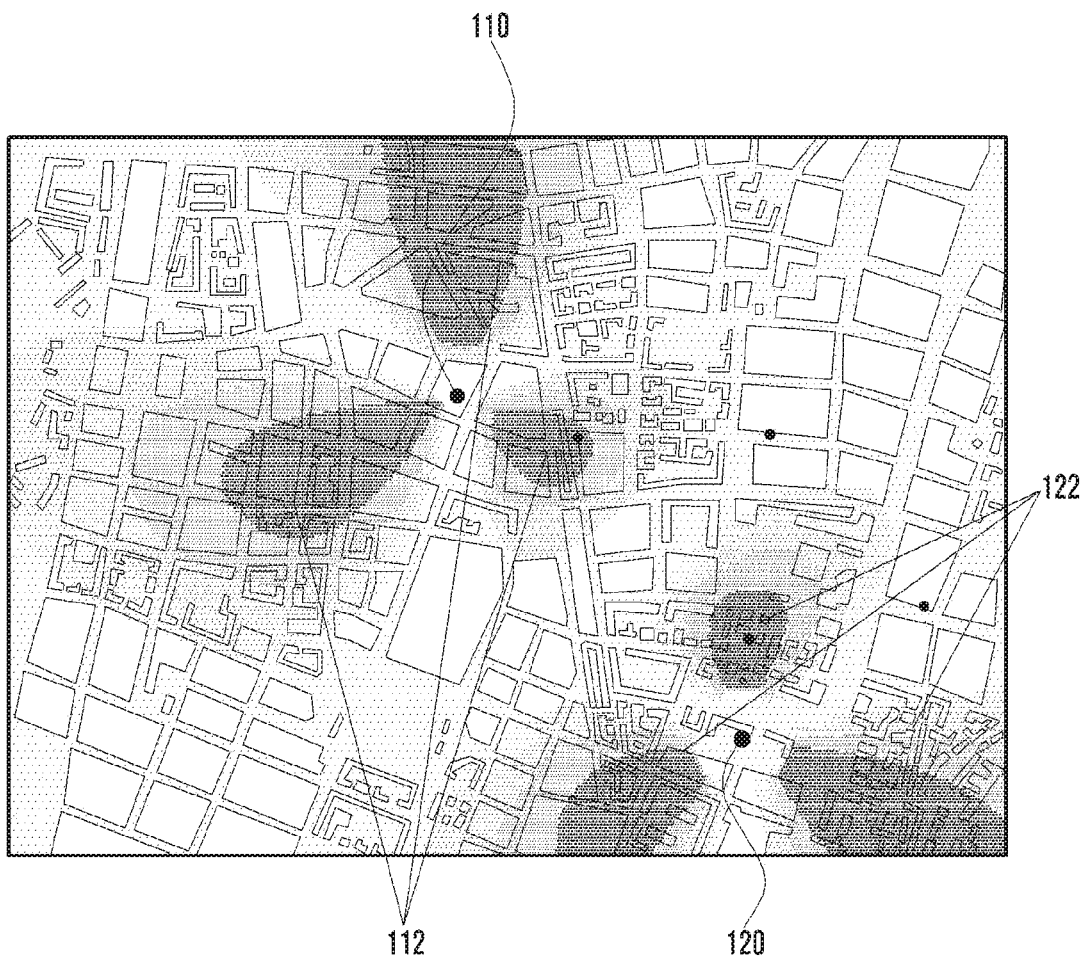
FIG. 1 illustrates network designing using a mathematical modeling technique to an embodiment of the disclosure.

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Descriptions of functions and structures well known in the art and not directly related to the disclosure may be omitted for clarity and conciseness without obscuring the subject matter of the disclosure.

In the drawings, some elements are exaggerated, omitted, or only outlined in brief, and thus may be not drawn to scale. The same or similar reference symbols are used throughout the drawings to refer to the same or like parts.

The aspects, features and advantages of certain embodiments of the disclosure will be more apparent from the following detailed description taken in conjunction with the accompanying drawings. The description of the various embodiments is to be construed as exemplary only and does not describe every possible instance of the disclosure. It should be apparent to those skilled in the art that the following description of various embodiments of the disclosure is provided for illustration purpose only and not for the purpose of limiting the disclosure as defined by the appended claims and their equivalents. The same reference symbols are used throughout the description to refer to the same parts.

Meanwhile, it is known to those skilled in the art that blocks of a flowchart (or sequence diagram) and a combination of flowcharts may be represented and executed by computer program instructions. These computer program instructions may be loaded on a processor of a general-purpose computer, special purpose computer or programmable data processing equipment. When the loaded program instructions are executed by the processor, they create a means for carrying out functions described in the flowchart. As the computer program instructions may be stored in a computer readable memory that is usable in a specialized computer or a programmable data processing equipment, it is also possible to create articles of manufacture that carry out functions described in the flowchart. As the computer program instructions may be loaded on a computer or a programmable data processing equipment, when executed as processes, they may carry out operation of functions described in the flowchart.

A block of a flowchart may correspond to a module, a segment or a code containing one or more executable instructions implementing one or more logical functions, or to a part thereof. In some cases, functions described by blocks may be executed in an order different from the listed order. For example, two blocks listed in sequence may be executed at the same time or executed in reverse order.

In the description, the word "unit", "module" or the like may refer to a software component or hardware component such as an FPGA or ASIC capable of carrying out a function or an operation. However, "unit" or the like is not limited to hardware or software. A unit or the like may be configured so as to reside in an addressable storage medium or to drive one or more processors. Units or the like may refer to software components, object-oriented software components, class components, task components, processes, functions, attributes, procedures, subroutines, program code segments, drivers, firmware, microcode, circuits, data, databases, data structures, tables, arrays or variables. A function provided by a component and unit may be a combination of smaller components and units, and may be combined with others to compose large components and units. Components and units may be configured to drive a device or one or more processors in a secure multimedia card.

Additionally, in a drawing depicting a specific method of an embodiment, the order of steps or operations does not necessarily correspond to the order of execution, and some operations may be executed in reverse order or in parallel. In one embodiment, some operations may be executed selectively.

FIG. 1 illustrates network designing using a mathematical modeling technique.

Referring to FIG. 1, the transmitters 110 and 120 may generate transmission beams 112 and 122 to transmit signals.

In a mathematical modeling technique, RF information can be predicted by inputting the frequency and distance information about the transmission signal to a function explicitly representing a specific signal transmission and reception model. As shown in FIG. 1, each transmitter 110 or 120 can generate beams 113 or 112 in three directions, and RF characteristics of the transmission signal can be applied accordingly through the modeling technique. Such a mathematical modeling technique can predict RF information with less computational load, but a method for accurate measurement is required at higher frequencies.

Figure 2:
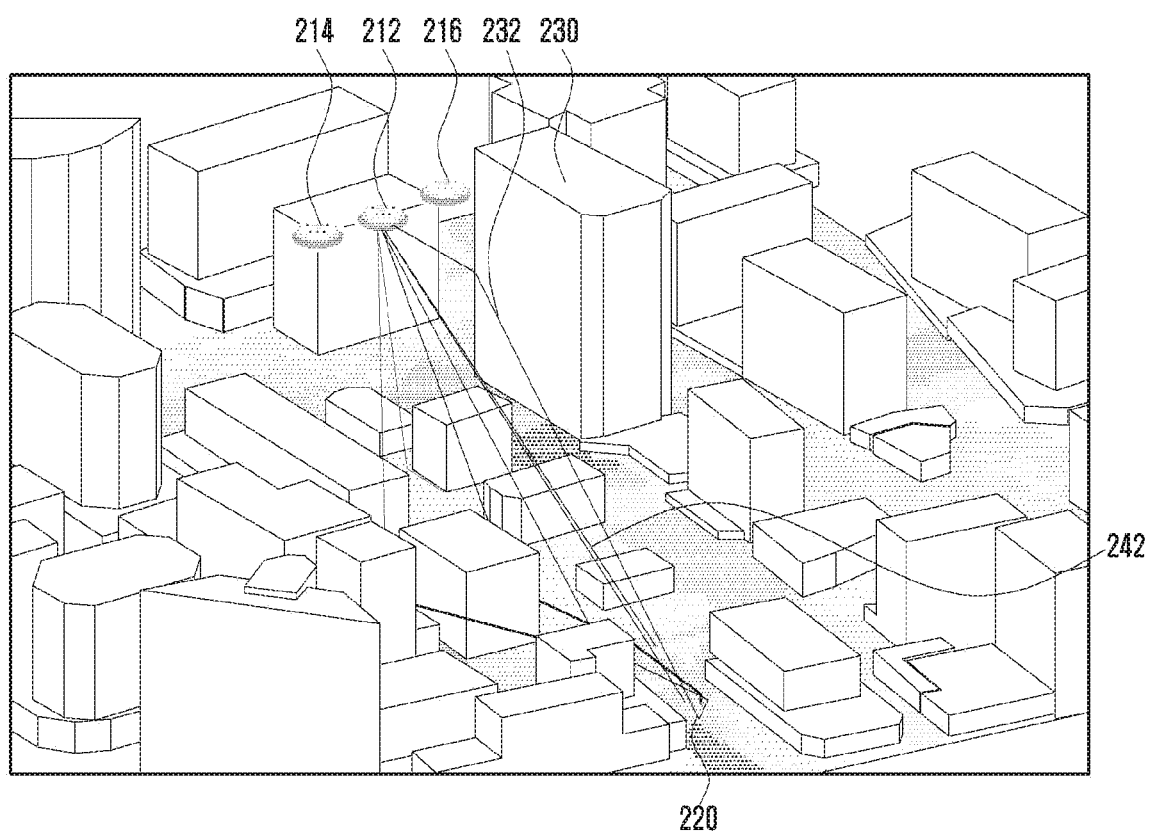
FIG. 2 illustrates a ray tracing simulation according to an embodiment of the disclosure.

FIG. 2 illustrates a ray tracing simulation according to an embodiment of the disclosure.

Referring to FIG. 2, assuming that one or more transmitters 212, 214 and 216 transmit signals, the strength of the signals transmitted by the transmitters 212, 214 and 216 is shown in light and shade on the map. The darker shade indicates stronger signal strength, and the lighter shade indicates weaker signal strength.

More specifically, based on the location of the receiver 220, it is possible to determine the reception strength of the signal in the corresponding region. It is possible to determine the transmission channel for each possible path from one of the transmitters 212, 214 and 216 to the receiver 220. There may be a signal 242 that is directly received by the receiver 220 from the transmitter 212 and a signal 232 that is reflected by an object 230 and is received by the receiver 220. By performing a simulation based on ray tracing, it is possible to obtain information about the reception strength of the signals from the transmitters 212, 214 and 216 in a specific region and the propagation paths of the signals. When determining the signal reception strength along the propagation path of the signal, the receiver 220 can obtain more accurate signal reception information if at least one of the surface material and the external shape of the signal reflecting object is considered. Here, the surface material does not only mean the outer surface of the object but also may include the inner material that may affect the reflection of the radio wave. Such information can be used to more accurately estimate the characteristics of radio wave reflection.

In addition, a radio wave-transmissible obstacle may be located on the path through which the signal is directly transmitted. An example of such an obstacle may be a tree. An obstacle that can transmit the radio wave but causes signal attenuation like a tree can be considered in the ray tracing simulation. More accurate simulation results can be obtained by considering information about the obstacles capable of transmitting the radio wave. Here, the tree is an example of an obstacle that is located on the signal propagation path and causes signal attenuation during radio wave transmission, may be a plant or a structure installed on the propagation path, and may also be another object that may cause signal attenuation.

By performing a ray tracing simulation in this way, at least one of the optimum transmitter position and the receiver position can be determined on the map. In one embodiment, the ray tracing simulation may be performed in consideration of a plurality of transmitter position candidates and receiver position candidates, and it is possible to determine at least one of the transmitter position and the receiver position according to the ray tracing results.

In this manner, the ray tracing simulation can be used to determine the transmission channel for each of the paths through which the RF signal passes, and predict RF signal information at the position of the receiver 220 based on the simulation results. In the process of determining the channel environment along the signal path, the ray tracing simulation may calculate at least one of the signal propagation distance, the environment of a path (e.g., type of the medium), and the effects of reflection and diffraction caused by the 3D terrain or buildings, thereby producing more accurate RF signal information. Additionally, the above channel estimation technique does not have any limitation due to the frequency of the RF signal, can accurately reflect the actual environment, and can be used to determine at least one of the optimal transmission position and the reception position based on the simulation results.

5G networks use very high frequency signals of 28 to 60 GHz. Hence, it is possible to improve accuracy in 5G network design by using a ray tracing simulation technique, not a mathematical modeling technique, to obtain radio signal information. In the ray tracing simulation, to estimate the reflected path of the radio wave due to a building, the reflection effect may be calculated by assuming that the surfaces of all buildings have the same RF characteristics. However, since the reflectance of the RF signal differs depending on the surface material, external shape and pattern of the reflection surfaces, this assumption does not guarantee accurate simulation results. Therefore, a ray tracing technique considering this information is required. Also, in the case of trees, when the frequency of the radio signal becomes high, they may substantially affect signal propagation. Accordingly, an analysis method considering trees is required.

In the following description, objects like trees may include herbaceous or woody plants that are located on radio signal propagation paths and may affect signal transmission. Unlike terrains and buildings, trees may be not included in the map information, and the locations of the trees may be determined through separate image analysis. The trees can substantially affect the transmission of high frequency radio signals. More specifically, the signal may be unable to pass through the trees, and may reflect, scatter, or diffract. Even when the signal passes through the trees, the signal attenuation may be larger compared with the case where the signal propagates in the air. As such, by considering the effect of trees on radio signal propagation, more accurate results can be obtained.

Figure 3:
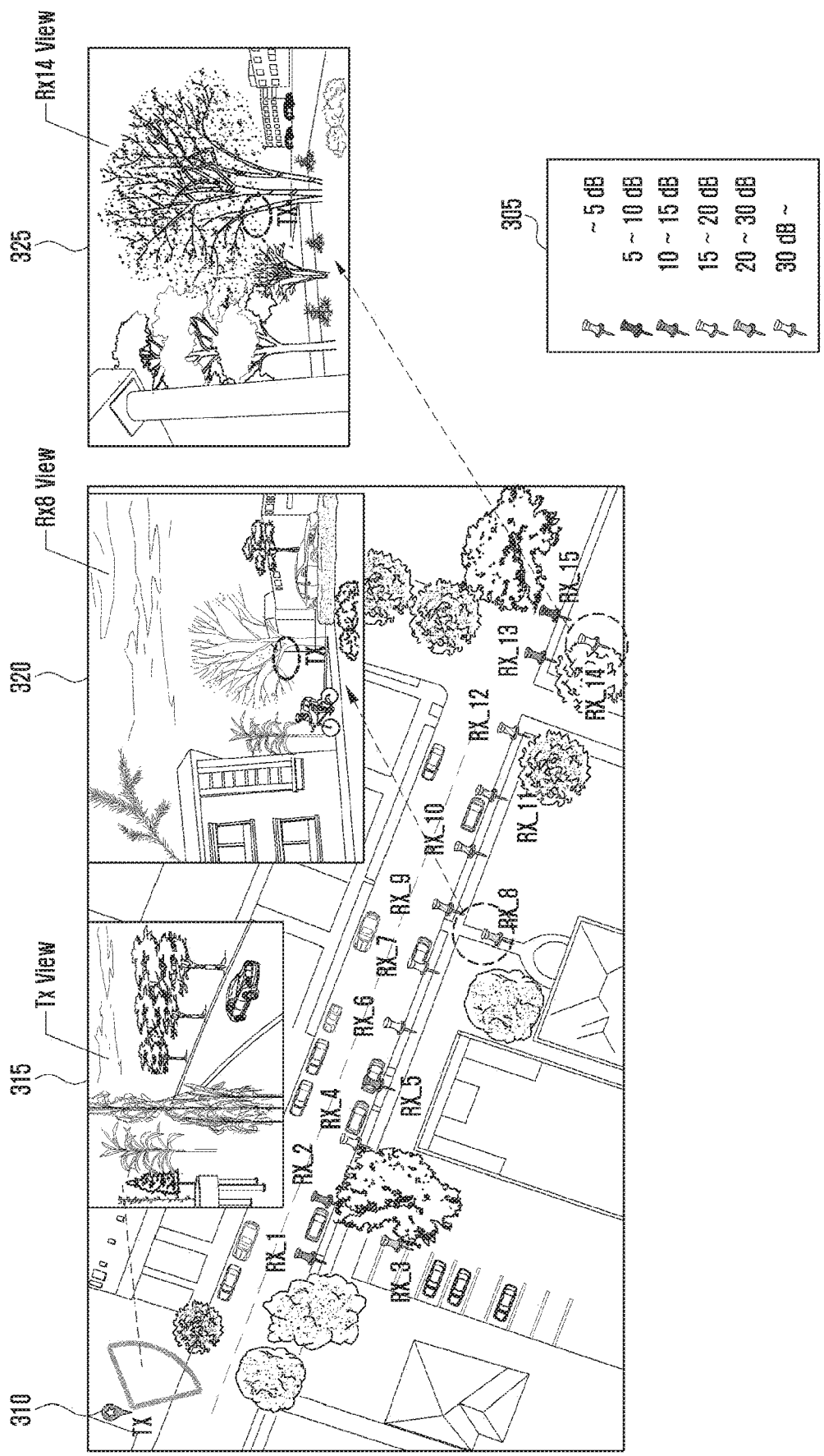
FIG. 3 illustrates a radio signal propagation environment between transmitters and receivers according to an embodiment of the disclosure.

FIG. 3 illustrates a radio signal propagation environment between transmitters and receivers according to an embodiment of the disclosure.

Referring to FIG. 3, the transmitter 310 may transmit a signal, and receivers (RX 1 to RX 15) may be located on the map. The point displayed at each receiver indicates how much signal attenuation has occurred in comparison to the attenuation of the radio signal transmitted by the transmitter in the absence of an obstacle.

The signal attenuation may become large when an obstacle is located on the path from the transmitter 310 to each receiver. Such an effect becomes larger as the frequency of the radio signal transmitted by the transmitter 310 becomes higher.

Reference numeral 315 denotes an image viewed from the transmitter 310 in the indicated direction. The trees existing in this case can act as an obstacle.

Reference numeral 320 denotes an image viewed from the RX 8 receiver to the transmitter 310. In this case, although a tree lies on the line of sight from the RX 8 receiver to the transmitter 310, the transmitter 310 is visible through the trunk of the tree. In such a case, the signal attenuation is not large.

Reference numeral 325 denotes an image viewed from the RX 14 receiver to the transmitter 310. In this case, a tree lies on the line of sight from the RX 14 receiver to the transmitter 310, and the crown (leaves and branches) of the tree is located on the line of sight. In such a case, the signal attenuation is large. However, although the crown of the tree is located on the line of sight, if the density of the leaves is low, radio signals can be substantially transmitted, and such circumstances need to be considered.

As described above, when a tree is located on the radio signal propagation path, the signal may be attenuated. More specifically, the portion of the tree located on the line of sight may determine the attenuation of the directly transmitted signal. Hence, to more accurately understand the radio signal propagation patterns, it is necessary to model the characteristics of trees and analyze the propagation pattern of the radio signal accordingly.

Figure 4:
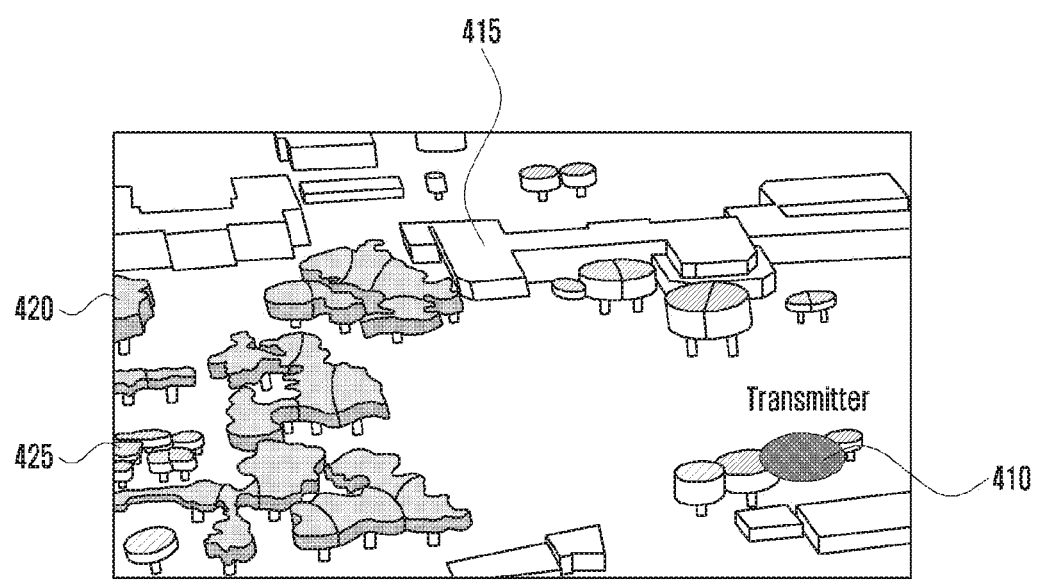
FIG. 4 illustrates an example of considering trees on the map according to an embodiment of the disclosure.

FIG. 4 illustrates an example of considering trees on the map according to an embodiment of the disclosure.

Referring to FIG. 4, the transmitter 410 may transmit a radio signal, and radio signal propagation patterns can be analyzed at individual locations on the map. A building 415 may be located on the map. In the case of a building, at least one of the location and height information may be indicated in the map information. As most buildings are made of materials that are difficult for the radio wave to penetrate, the radio signal propagation pattern may be analyzed in consideration of this.

In addition, trees 420 and 425 may be located on the map. The trees 420 and 425 can be classified into a dense tree 420 and a sparse tree 425 according to the density of leaves. The influence of the leaf distribution on the radio signal propagation may be different, and the propagation pattern of the radio signal can be analyzed in consideration of this.

In the case of a tree 420 or 425, it is also possible to analyze the influence of the tree on the radio signal propagation by dividing the tree into the trunk and the crown (leaves and branches). That is, it is possible to more accurately analyze radio signal propagation patterns by modeling the tree in terms of trunk and crown.

In one embodiment, information on the trees can be obtained through aerial images and tree distribution data. It is possible to determine the tree characteristics by considering the average distribution of trees in a specific area. For example, it is possible to acquire image information through aerial photographing or street photographing and identify the area where a tree is present based on the image information.

In embodiments of the disclosure, the characteristics of each tree in a region where trees are present can be modeled so as to more accurately analyze the radio signal propagation patterns.

Figure 5:
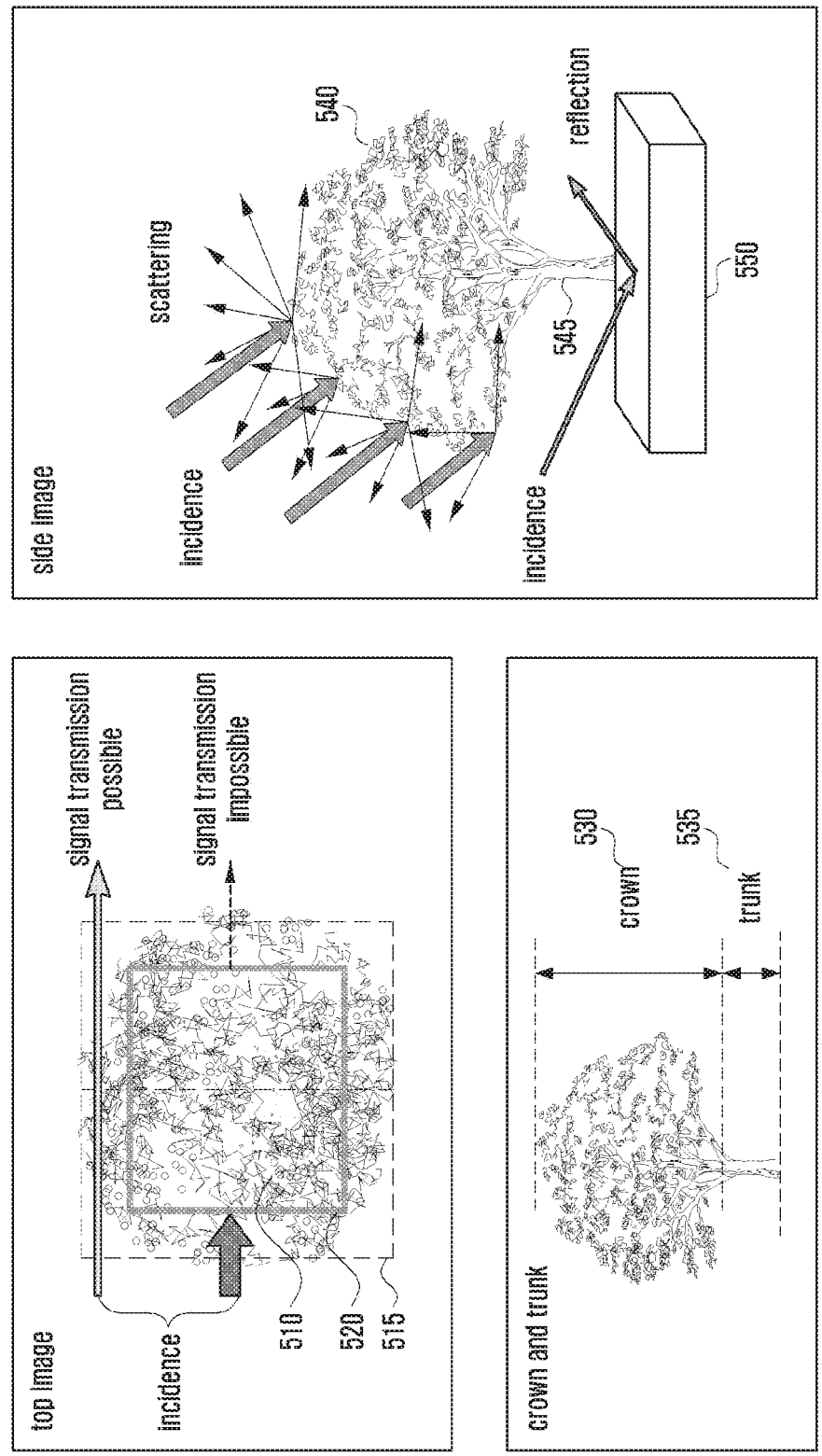
FIG. 5 depicts radio signal propagation characteristics of individual parts of a tree according to an embodiment of the disclosure.

FIG. 5 depicts radio signal propagation characteristics of individual parts of a tree according to an embodiment of the disclosure.

FIG. 5 depicts a scheme for analyzing radio signal propagation characteristics in consideration of trees.

Referring to FIG. 5, the top image can be obtained through an image taken in the sky such as an aerial view. The radio signal may be incident on the left side of the drawing. Here, among the entire region 515 in which the tree is located, the portion 510 with dense leaves does not transmit the radio signal and may block the signal. This leafy portion is indicated by reference numeral 520. Normally, such a leafy portion can occupy 60 to 90 percent of the region occupied by the whole tree. These numerical values are for example only, and may vary depending on the types of trees.

In one embodiment, the region occupied by the whole tree may be identified, and 60 to 90 percent of the identified tree region at the center thereof may be identified as the region where signal transmission is not possible. The size of the region where signal transmission is not possible may be determined based on the obtained image or the tree distribution in the corresponding area. More specifically, when a dense tree is located on the image, the size of the region where signal transmission is not possible can be increased. Also, when a large number of leafy trees are present in a specific area, the size of the region where signal transmission is not possible can be increased.

In a certain embodiment, there is a need to distinguish between the vertical regions occupied by the crown and the trunk. The region 530 occupied by the crown and the region 535 occupied by the trunk can be distinguished as shown in the drawing. This distinction can be made based on image information like a street view, and their corresponding heights can be determined based on the general characteristics of the trees in the corresponding area. By distinguishing between the region 530 occupied by the crown 530 and the region 535 occupied by the trunk 535, different influences on radio signal transmission can be analyzed.

For the side image in FIG. 5, when the signal is incident, scattering may occur in the crown portion 540, and the signal may be transmitted or reflected by the ground 550 in the trunk portion 545. Although not shown, in the crown portion 540, some transmission may occur, and diffraction may also occur. Also, in the trunk portion 540, scattering, transmission and diffraction can affect signal transmission. In the region indicated by reference numeral 520, signal transmission may occur. Here, signal attenuation may occur in proportion to the length of the transmission path. It is possible to consider both such attenuation and the transmitted signal component reaching the receiver.

Figure 6:
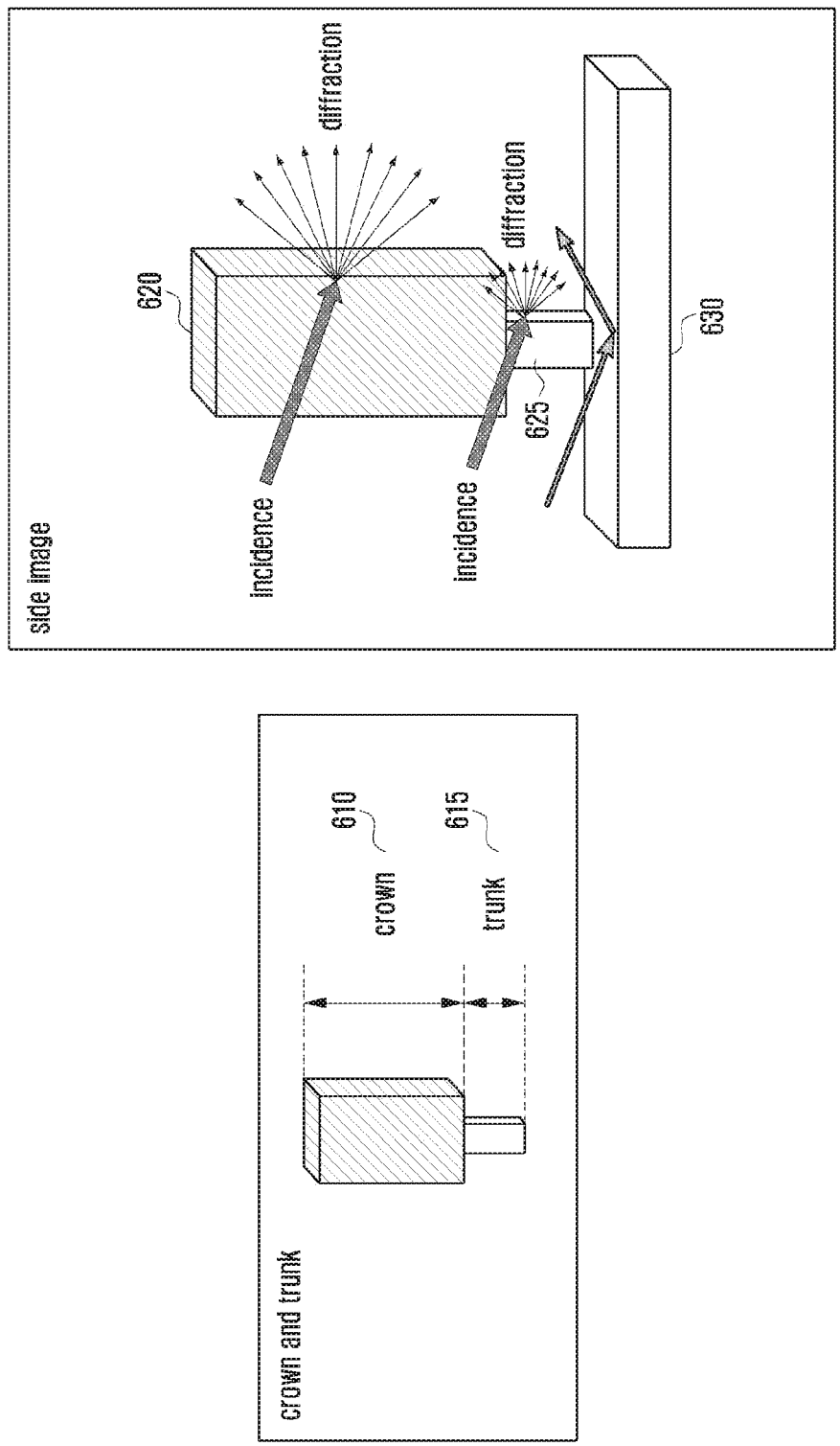
FIG. 6 illustrates modeling of a tree and depicts radio signal propagation characteristics in the modeled tree according to an embodiment of the disclosure.

FIG. 6 illustrates modeling of a tree and depicts radio signal propagation characteristics in the modeled tree according to an embodiment of the disclosure.

Referring to FIG. 6, the tree can be modeled in a shape corresponding to the region affecting radio signal transmission in the area where the crown and trunk of the tree are located. For ease of description, the crown portion 610 and the trunk portion 615 are respectively modeled as square pillars, but they can be modeled as different pillars according to the actual shape of the tree. The regions occupied by the quadrangular pillars can be determined by the scheme described in the previous embodiment.

As shown by the side image of FIG. 6, to analyze the radio signal propagation patterns, it is possible to consider the diffraction occurring at each corner of the crown portion 620 and the trunk portion 625. In the case of the ground 630, the reflection characteristics may be considered. Although not shown, the effects of reflection, transmission, and scattering can also be taken into account at a specific location. Diffraction can also occur at a portion other than the corner, and a method for considering such characteristics will be described later.

Figure 7:
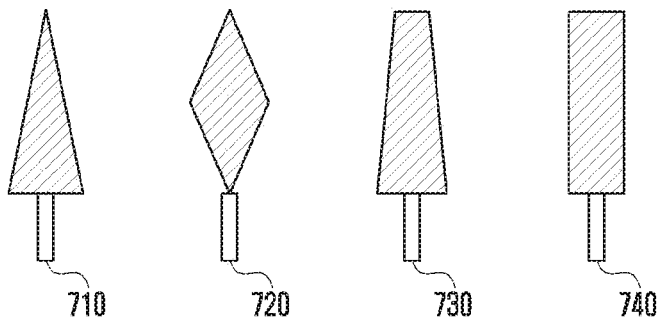
FIG. 7 depicts an example of modeling the shape of tree leaves according to an embodiment of the disclosure.

FIG. 7 depicts an example of modeling the shape of tree leaves according to an embodiment of the disclosure.

Referring to FIG. 7, the crown and the trunk of a tree can be modeled as one of the shapes indicated by reference numerals 710, 720, 730, and 740. After modeling, the corresponding physical values can be assigned to the modeled portions. By selecting a model corresponding to the tree and applying it to the simulation, it is possible to obtain results similar to the actual radio signal propagation situation with a smaller amount of computation. In the case of the shape, the tree can be modeled as a similar shape on the basis of the tree information obtained through image data.

In one embodiment, the tree can be modeled as a prism shape or pyramid shape. The number of shapes for tree modeling may vary depending on the situation, and the modeling scheme may be determined based on the distribution of the tree species in the area where the simulation is performed for. In another embodiment, the tree can be modeled as a cylindrical shape.

Figure 8:
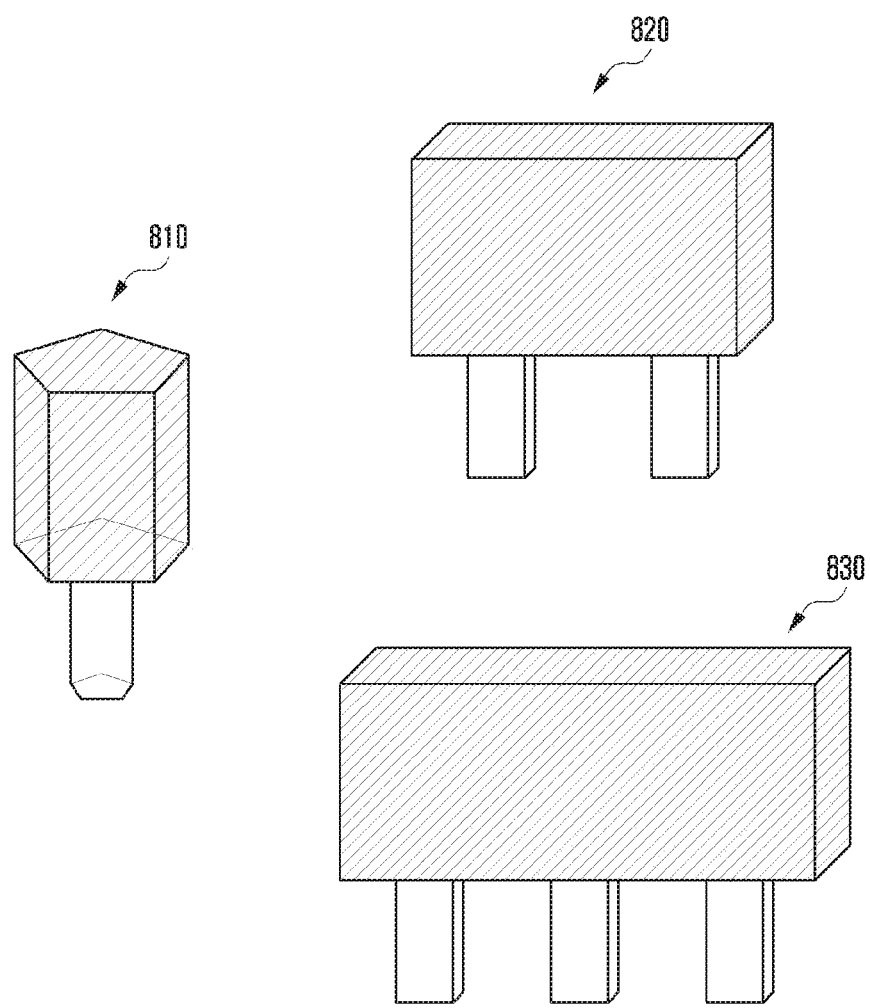
FIG. 8 depicts an example of modeling a tree according to an embodiment of the disclosure.

FIG. 8 depicts an example of modeling a tree according to an embodiment of the disclosure.

Referring to FIG. 8, the tree can be modeled as a pentagonal pole as indicated by reference numeral 810. Here, only the crown portion can be modeled as a pentagonal pole, and the trunk portion can also be modeled as a pentagonal pole. In one embodiment, the tree may be modeled as an N-sided polygonal pole (N is a natural number) approximating the actual shape of the tree.

As indicated by reference numeral 820 or 830, if there are adjacent trees, all the crown portions can be modeled as an N-sided polygonal pole, and the trunk portions can be added in proportion to the number of trees. If there are many adjacent trees, it may be difficult to determine the number of trunks based on image information. In this case, the number of trunks can be determined in proportion to the size of the region occupied by all the tree leaves or crowns. Here, it can be assumed that the trunks are arranged at a uniform density over the corresponding region. It can also be assumed that the trunks are arranged more densely toward the outside of the area where the leaves are located.

It is possible to obtain more accurate results by simulating the radio signal propagation patterns after modeling the crown and trunk of a tree as described above.

Figure 9:
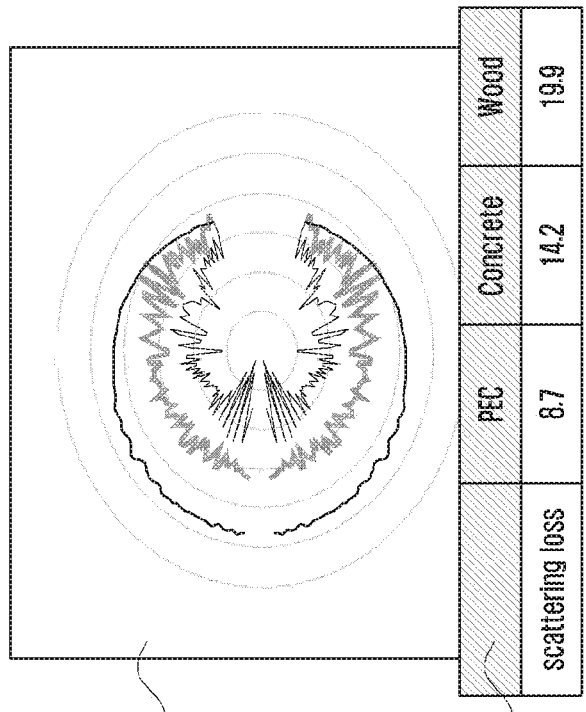
FIG. 9 illustrates signal propagation patterns according to scattering of the radio signal by material and size to an embodiment of the disclosure.
Figure 9:
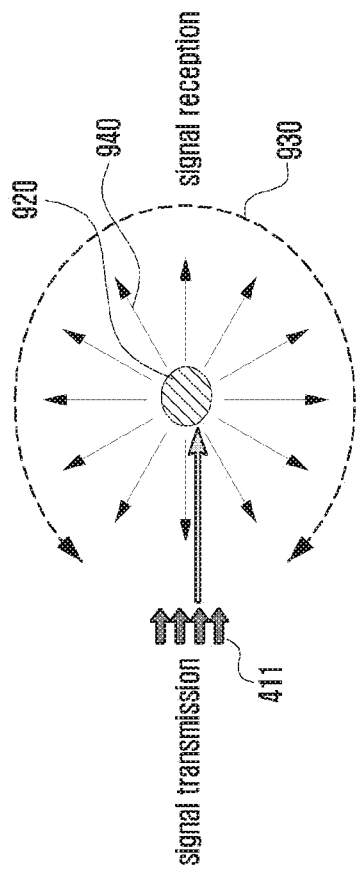
Figure 9:
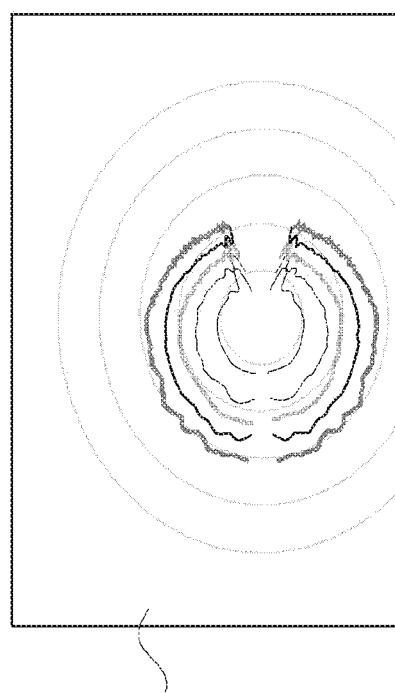

FIG. 9 illustrates signal propagation patterns according to scattering of the radio signal by material and size.

Referring to FIG. 9, when a radio signal is incident on an object having a specific thickness, signal components are scattered in all directions from the object. Here, the scattering loss may vary depending on the thickness and material of the object.

As shown in part (a) of FIG. 9, when a radio signal is incident on the object 920 having a specific thickness in a direction indicated by reference numeral 411, the incident signal may be partially lost due to the scattering effect and scattered signal components (e.g., 940) may be received in the vicinity 930. It is necessary to consider such effects when analyzing the radio signal propagation patterns.

In part (b) of FIG. 9, the scattering loss values corresponding to the diameter of the object are shown as indicated by reference numerals 950 and 955. More specifically, the loss of the scattered signal component increases with the decreasing diameter, and the magnitude of the scattered signal component received in the vicinity increases with the increasing diameter. The difference between the scattering loss due to modeling and the actual measured scattering loss is shown as indicated by reference numeral 955.

In part (c) of FIG. 9, the scattering loss values according to the material of the object having a specific thickness are shown as indicated by reference numerals 960 and 965. More specifically, when the object having a certain thickness is made of a perfect electric conductor (PEC), concrete and wood, the loss values applied in omnidirectional scattering are shown. As shown, the scattering loss becomes larger in the order of the perfect electric conductor, concrete, and wood. The crown portion of a tree may have scattering loss characteristics similar to those of a perfect electric conductor, and the simulation can be performed by using this information. The difference in scattering loss values between the individual materials is shown as indicated by reference numeral 965.

When a radio signal is transmitted, omnidirectional scattering may occur with a specific loss depending on the thickness and material of the object located on the transmission path. Hence, the simulation can be performed by applying the above characteristics to the modeled tree.

Figure 10:
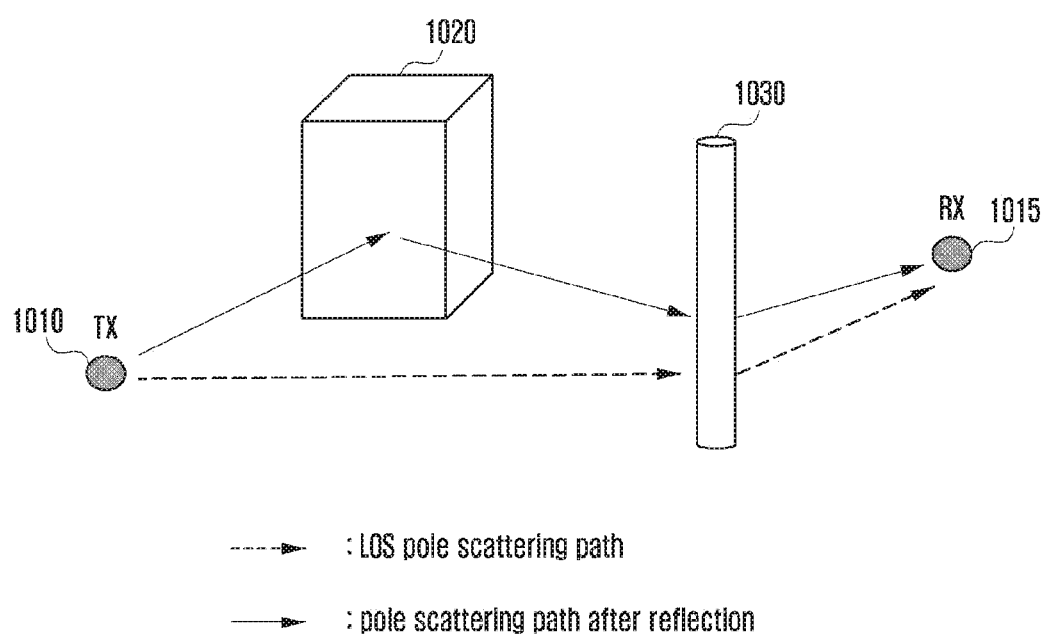
FIG. 10 illustrates propagation paths due to reflection and scattering to an embodiment of the disclosure.

FIG. 10 illustrates propagation paths due to reflection and scattering.

In FIG. 10, at least one of the paths through which the radio signal is transmitted from the transmitter 1010 to the receiver 1015 is shown. More specifically, the signal propagation paths affected by the building 1020 and the pole 1030 are shown.

The radio signal emitted by the transmitter 1010 may propagate along the line of sight path, and be scattered by the pole 1030 and received by the receiver 1015. In this case, the strength of the signal received by the pole 1030 may be computed in consideration of the distance from the transmitter 1010 to the pole 1030, and the characteristics of the scattered signal component determined based on the thickness and material of the pole 1030 may be applied.

In addition, the radio signal emitted by the transmitter 1010 may be reflected by the building 1020, be scattered by the pole 1030, and be received by the receiver 1015. In this case, the strength of the signal received by the pole 1030 may be computed in consideration of at least one of the distance from the transmitter 1010 to the building 1020, the distance from the building 1020 to the pole 1030, the angle of the signal incident on the building 1020, and the material of the building 1020, and the characteristics of the scattered signal component determined based on the thickness and material of the pole 1030 may be applied.

As described above, by analyzing the characteristics of the scattered signal component in consideration of the line of sight transmission path and the reflected transmission path, it is possible to more accurately simulate the radio signal propagation.

Figure 11:
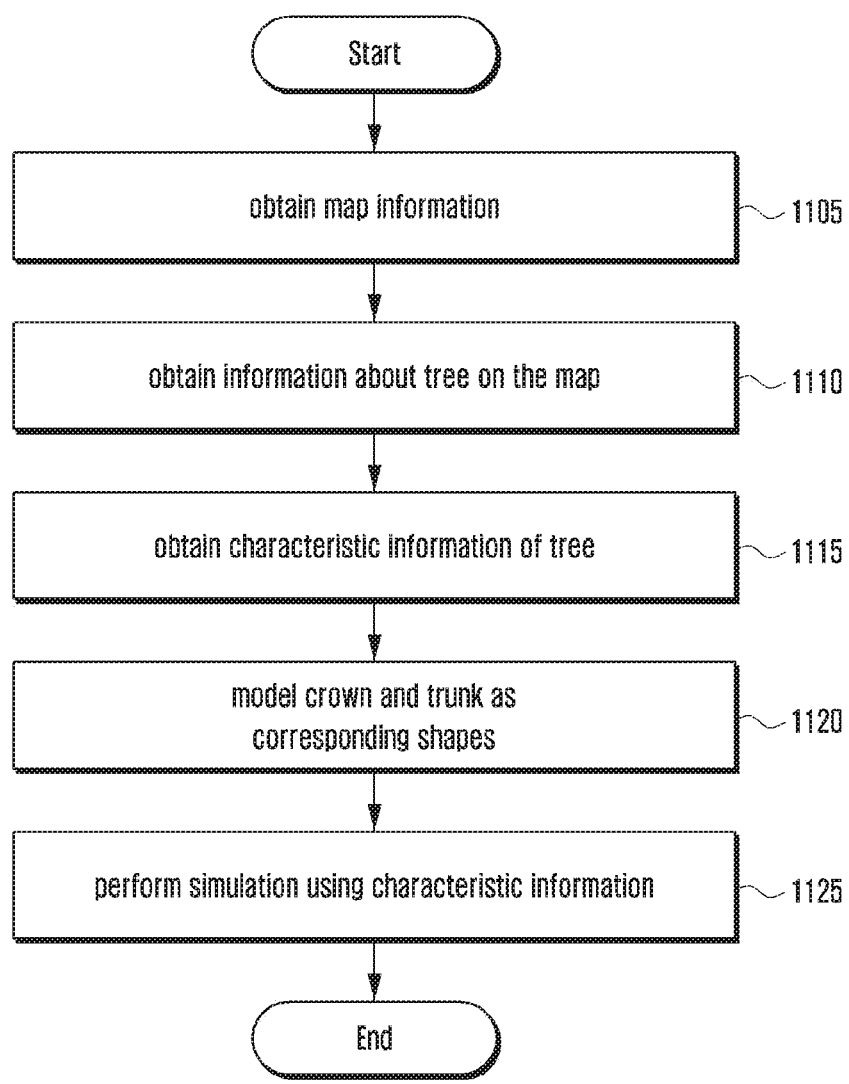
FIG. 11 is a flowchart of a method for simulating radio signal propagation in consideration of the characteristics of a tree according to an embodiment of the disclosure.

FIG. 11 is a flowchart of a method for simulating radio signal propagation in consideration of the characteristics of a tree according to an embodiment of the disclosure.

Referring to FIG. 11, the computing device may obtain information about the signal propagation, the map, and the trees on the map, and simulate the radio signal propagation pattern based on the obtained information.

At operation 1105, the computing device may obtain map information. More specifically, the computing device may obtain at least one of two-dimensional and three-dimensional map information. The map information may include at least one of the terrain information and building related information, and may further include information about the characteristics of a specific area if necessary. More specifically, the characteristic information may include information about the use of the specific area, and may further include information about the area where trees can be present. The characteristic information may also include information about the use of a specific area such as roads or sidewalks.

At operation 1110, the computing device may obtain tree information on the map. The tree information may include information about the location of a tree and the size of the region occupied by the tree, and may be obtained based on the image information such as an aerial view and a street view. The tree information may further include information about the location and characteristics of the trees obtained from an external database. If the tree information is acquired from the image information, the position of the tree can be marked on the map accordingly.

At operation 1115, the computing device may obtain the characteristic information of the tree. More specifically, the computing device can identify the region that may substantially affect radio signal propagation based on the region where the crown is located. In addition, the computing device can identify information on the trunk. More specifically, the computing device can identify the location of the trunk in accordance with the region where the crown is located. In one embodiment, the characteristic information of the tree may include information about the density of the leaves and the thickness of the trunk. The characteristic information of the tree may also include information about the heights of the crown portion and the trunk portion.

At operation 1120, the computing device may model the crown and the trunk as corresponding shapes based on the obtained information. For example, the modeling shape may be an n-sided polygonal pole corresponding to the region occupied by the actual crown and trunk. The modeling shape may also be a horn shape. The modeling shapes may be arranged on the map. In addition, the physical characteristic information may also be assigned to the modeled crown and trunk. The characteristic information may include information related to reflectance and transmittance corresponding to the modeling shape, and further include diffraction related information.

At operation 1125, the computing device may perform simulation on the propagation of the radio signal from the transmitter to the receiver on the basis of the characteristic information obtained at the previous operation. It is possible to analyze the radio signal propagation patterns in more detail through simulation.

Figure 12:
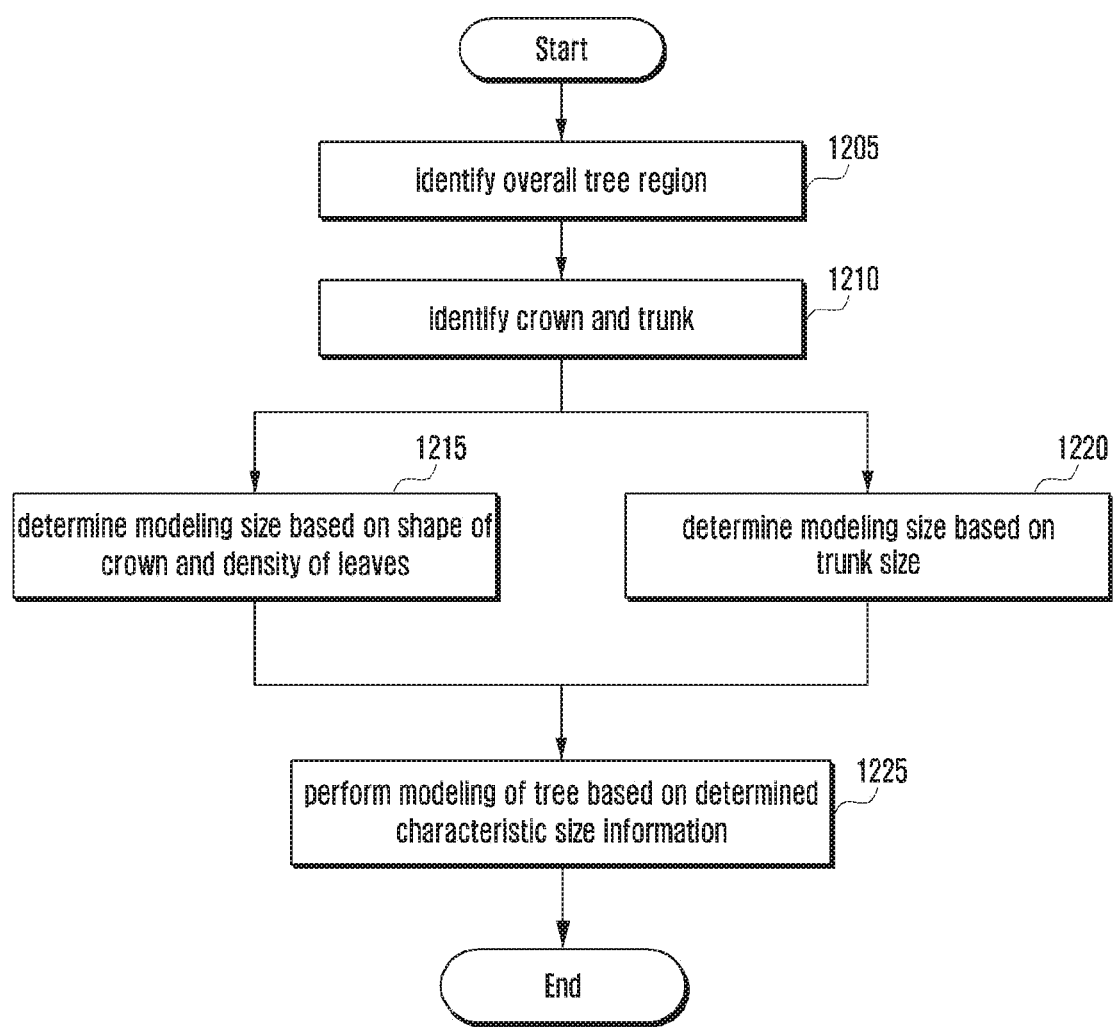
FIG. 12 is a flowchart of a method for modeling the shape of a tree according to an embodiment of the disclosure.

FIG. 12 is a flowchart of a method for modeling the shape of a tree according to an embodiment of the disclosure.

Referring to FIG. 12, the computing device can identify information for tree shape modeling and perform modeling accordingly.

At operation 1205, the computing device may identify the overall tree region. For example, the computing device can identify the region where the tree is present based on image information or an external database.

At operation 1210, the computing device may identify the regions occupied by the crown and the trunk in the overall tree region. More specifically, the region where the crown is located and the region where the trunk is located can be identified. Such region identification may be performed based on image information, and may also be performed based on representative distribution information of the trees in the corresponding area.

At operation 1215, the computing device may determine the region affecting signal transmission based on at least one of the shape and density of the leaves among the crown region. More specifically, although some leaves are present at the outer portion of the region where the leaves are present, the influence of the outer portion on the signal transmission is small. Hence, it is necessary to identify the portion that can substantially affect signal transmission. This may be performed through image analysis or may be performed by selecting 60 to 90 percent of the entire region where the leaves are present with respect to the center thereof.

At operation 1220, the computing device may determine the modeling size according to the size of the trunk. This may include checking the trunk size through image analysis. The trunk size may be determined in accordance with the crown size without separate checking. In this case, the characteristics of the trees in the corresponding area can be considered.

At operation 1225, the computing device may model the crown portion and the trunk portion based on the determined modeling size. As such, it is possible to identify the signal transmission characteristics based on the modeled crown and trunk.

Figure 13:
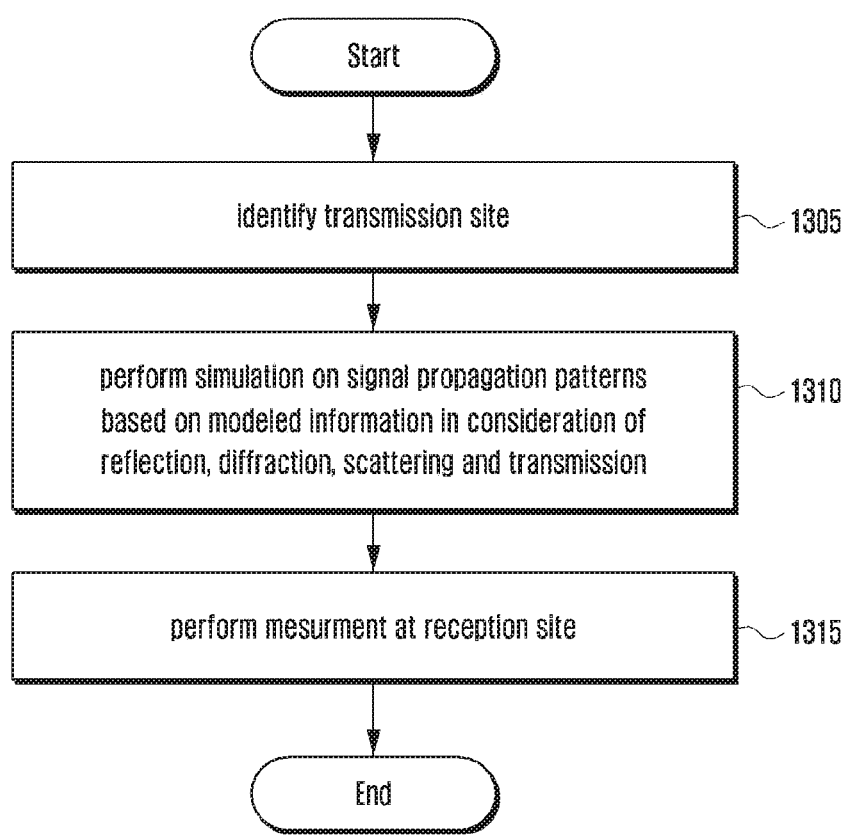
FIG. 13 is a flowchart of a method for simulating radio signal propagation in consideration of the characteristics of a tree according to an embodiment of the disclosure.

FIG. 13 is a flowchart of a method for simulating radio signal propagation in consideration of the characteristics of a tree according to an embodiment of the disclosure.

Referring to FIG. 13, the computing device can analyze the radio signal propagation patterns based on information about the modeled tree.

At operation 1305, the computing device may identify the transmission site (or, a location or a position) and obtain information on the characteristics of the radio signal transmitted from the transmission site. More specifically, the computing device can obtain information about at least one of the frequency and beamforming of the transmitted signal. Thereafter, the computing device can perform the simulation in consideration of this information.

At operation 1310, the computing device may analyze the radio signal propagation patterns on the basis of the map information and the tree information modeled on the map.

More specifically, the computing device can analyze signal propagation patterns by applying at least one of reflection, diffraction, scattering, and transmission to the map information and modeled tree information.

At operation 1315, the computing device may calculate measurement values of the signal received at the reception site (or, a location or a position) on the basis of the analyzed signal propagation patterns. Hence, by analyzing the radio signal propagation patterns in consideration of the map information and modeled tree information, it is possible to obtain measurement results similar to actual ones with a smaller amount of computation.

Figure 14:
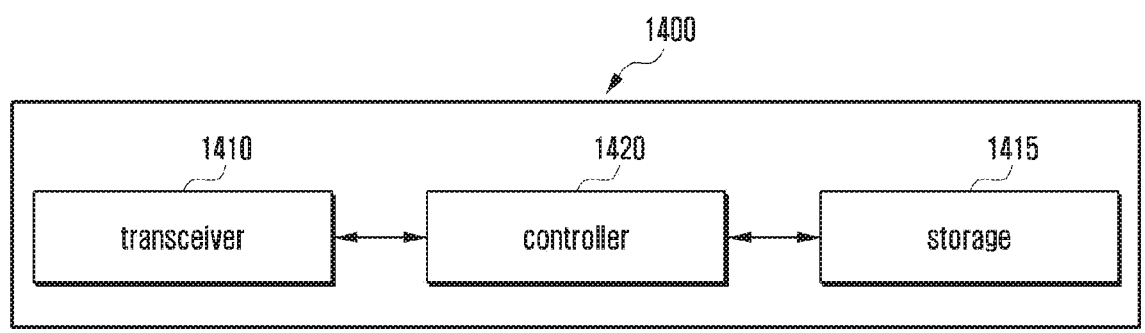
FIG. 14 is a block diagram of a computing device according to an embodiment of the disclosure.

FIG. 14 is a block diagram of a computing device according to an embodiment of the disclosure.

FIG. 14 shows the computing device according to an embodiment of the disclosure.

Referring to FIG. 14, the computing device 1400 may include a transceiver 1410, a storage 1415 (e.g., a memory), and a controller 1420 (e.g., at least one processor).

The transceiver 1410 may transmit and receive a signal to and from an external device outside the computing device 1400. More specifically, the transceiver 1410 can transmit and receive data to and from the external device, and can include an interface therefor.

The storage 1415 may store at least one of information related to the computing device 1400 and information transmitted and received through the transceiver 1410. The storage 1415 may also store the overall information required for the simulation in embodiments of the disclosure, such as information on the simulation results, information on the object surface material and external shape obtained through image analysis, information on the three-dimensional map information, information on the surface material and external shape of the object marked on the map, and information on the modeled tree. In one embodiment, the storage 1415 may store the characteristic information of the tree located on the map and information for modeling the tree. Based on at least one of the simulation result and the comparison result, new information may be added to the information stored in the storage 1415, and some thereof may be deleted or updated.

The controller 1420 can control the operation of the computing device 1400 and can control the computing device 1400 to perform operations required by the embodiments described before. The controller 1420 may include at least one processor. The processor may be controlled by a program that is composed of instructions to perform the method described in the embodiments of the disclosure. The program may be stored in a storage medium, and the storage medium may include a volatile or non-volatile memory. The memory may be a medium capable of storing data, and there is no restriction on the form of the memory when the instructions can be stored in the memory.

While the disclosure has been described with reference to various embodiments thereof it will be understood by those skilled in the art that various changes in form and details may be made therein without departing from the spirit and scope of the disclosure as defined by the appended claims and their equivalents.

What is claimed is:

1. A method for identifying radio signal transmission characteristics in a wireless communication system, the method comprising:
identifying a signal transmission location;
identifying a signal reception location;
identifying an area where a tree is present between the signal transmission location and the signal reception location;
identifying a characteristic of a crown of the tree and a characteristic of a trunk of the tree;
determining a transmission characteristic of a radio signal sent from the signal transmission location to the signal reception location based on the characteristic of the crown and the characteristic of the trunk;
finding one or more models corresponding to a shape of the tree; and
selecting one of the corresponding models based on the characteristic of the crown and the characteristic of the trunk,
wherein the transmission characteristic of the radio signal is determined based on the selected corresponding model.

2. The method of claim 1,
wherein the identifying of the characteristic of the crown and the characteristic of the trunk comprises:
identifying a size of a first region where the crown is located; and
identifying a size of a second region that can affect a radio signal propagation within the first region, and
wherein the transmission characteristic of the radio signal is determined based on a characteristic of the second region.

3. The method of claim 1,
wherein the characteristic of the trunk is determined based on a region where the crown of the tree is located, and
wherein the method further comprises:
modeling at least one of the crown or the trunk as a pole with a corresponding size based on the characteristic of the crown and the characteristic of the trunk.

4. The method of claim 1, further comprising:
identifying a position of at least one pole located between the signal transmission location and the signal reception location,
wherein the determining of the transmission characteristic of the radio signal comprises determining a transmission characteristic of the radio signal transmitted to the reception location by considering an effect of at least one of reflection, diffraction, or scattering occurring at a surface of the pole, and
wherein a material of the pole includes at least one of metal, concrete, or wood.

5. The method of claim 4, wherein the transmission characteristic of the radio signal is determined in consideration of a propagation effect caused by signal components passing through the pole or being reflected or diffracted at the surface of the pole.

6. The method of claim 1,
wherein the characteristic of the crown is determined based on a material characteristic of leaves of the tree, and
wherein the characteristic of the trunk is determined based on a material characteristic of the trunk of the tree.

7. The method of claim 1,
wherein the characteristic of the crown of the tree includes a first thickness of the crown in a direction of signal propagation,
wherein the characteristic of the trunk of the tree includes a second thickness of the trunk in the direction of signal propagation, and wherein the transmission characteristic of the radio signal is identified according to a scattering characteristic determined based on at least one of the first thickness or the second thickness.

8. The method of claim 7, wherein the scattering characteristic is determined based on a first signal component received directly from the transmission location and a second signal component received through at least one of reflection, transmission, or diffraction caused by at least one object.

9. The method of claim 1, wherein the characteristic of the crown and the characteristic of the trunk of the tree are identified based on average characteristics of trees existing in an area including the transmission location and the reception location.

10. A computing device capable of identifying signal transmission characteristics in a wireless communication system, comprising:
a transceiver for transmitting and receiving information; and
at least one processor connected with the transceiver and configured to:
identify a signal transmission location,
identify a signal reception location,
identify an area where a tree is present between the signal transmission location and the signal reception location,
identify a characteristic of a crown of the tree and a characteristic of a trunk of the tree,
determine a transmission characteristic of a radio signal sent from a signal transmission location to the signal reception location based on the characteristic of the crown and the characteristic of the trunk,
find one or more models corresponding to a shape of the tree, and
select one of the corresponding models based on the characteristic of the crown and the characteristic of the trunk,
wherein the transmission characteristic of the radio signal is determined based on the selected corresponding model.

11. The computing device of claim 10,
wherein the at least one processor is further configured to:
identify a size of a first region where the crown is located, and
identify a size of a second region that can affect a radio signal propagation within the first region, and
wherein the transmission characteristic of the radio signal is determined based on a characteristic of the second region.

12. The computing device of claim 10,
wherein the characteristic of the trunk is determined based on a region where the crown of the tree is located, and
wherein the at least one processor is further configured to model at least one of the crown or the trunk as a pole with a corresponding size based on the characteristic of the crown and the characteristic of the trunk of the tree.

13. The computing device of claim 10,
wherein the at least one processor is further configured to:
identify a position of at least one pole located between the signal transmission location and the signal reception location, and
identify a transmission characteristic of the radio signal transmitted to the reception location by considering an effect of at least one of reflection, diffraction, or scattering occurring at a surface of the pole, and
wherein a material of the pole includes at least one of metal, concrete, or wood.

14. The computing device of claim 13, wherein the transmission characteristic of the radio signal is determined in consideration of a propagation effect caused by signal components passing through the pole or being reflected or diffracted at the surface of the pole.

15. The computing device of claim 10,
wherein the characteristic of the crown is determined based on a material characteristic of leaves of the tree, and
wherein the characteristic of the trunk is determined based on a material characteristic of the trunk of the tree.

16. The computing device of claim 10,
wherein the characteristic of the crown of the tree includes a first thickness of the crown in a direction of signal propagation,
wherein the characteristic of the trunk of the tree includes a second thickness of the trunk in the direction of signal propagation, and
wherein the transmission characteristic of the radio signal is identified according to a scattering characteristic determined based on at least one of the first thickness or the second thickness.

17. The computing device of claim 16, wherein the scattering characteristic is determined based on a first signal component received directly from the transmission location and a second signal component received through at least one of reflection, transmission, or diffraction caused by at least one object.

18. The computing device of claim 10, wherein the characteristics of the crown and the characteristic of the trunk of the tree are identified based on average characteristics of trees existing in an area including the transmission location and the reception location.

* * * * *